US005447854A

United States Patent [19]
Goto et al.

[11] Patent Number: 5,447,854
[45] Date of Patent: Sep. 5, 1995

[54] PRODUCTION OF CYCLOSPORIN A AND/OR C WITH A STRAIN OF NECTRIA

[75] Inventors: Toshio Goto, Kobe; Toru Kino, Tsuchiura; Masakuni Okuhara, Tsukuba; Hirokazu Tanaka, Takarazuka; Yasuhisa Tsurumi, Tsukuba; Shigehiro Takase, Ibaraki, all of Japan

[73] Assignee: Fujisawa Pharmaceutical Co., Ltd., Osaka, Japan

[21] Appl. No.: 90,138

[22] PCT Filed: Jan. 22, 1992

[86] PCT No.: PCT/JP92/00047
§ 371 Date: Nov. 10, 1993
§ 102(e) Date: Nov. 10, 1993

[87] PCT Pub. No.: WO92/13094
PCT Pub. Date: Aug. 6, 1992

[30] Foreign Application Priority Data
Jan. 25, 1991 [JP] Japan .................. 3-87151

[51] Int. Cl.⁶ .................. C12P 21/04; C12N 1/14
[52] U.S. Cl. .................. 435/71.3; 435/71.1; 435/254.1
[58] Field of Search .................. 435/71.1, 71.3, 71.2, 435/259, 254.1

[56] References Cited

U.S. PATENT DOCUMENTS

| | | | |
|---|---|---|---|
| 4,108,985 | 8/1978 | Rüegger et al. | 424/177 |
| 4,330,560 | 5/1982 | Staron et al. | 435/251 |
| 5,051,402 | 9/1991 | Kurihara et al. | 514/11 |
| 5,156,960 | 10/1992 | Jekkel | 435/71.1 |
| 5,214,130 | 5/1993 | Patchett et al. | 530/333 |
| 5,256,547 | 10/1993 | Rudat et al. | 435/71.1 |

FOREIGN PATENT DOCUMENTS

| | | |
|---|---|---|
| 50-89598 | 7/1975 | Japan . |
| 52-59180 | 5/1977 | Japan . |
| 53-139789 | 12/1978 | Japan . |
| 55-55150 | 4/1980 | Japan . |
| 57-63093 | 4/1982 | Japan . |

OTHER PUBLICATIONS

ATCC Catalogue of Funji/Yeohi, 17th Ed, 1987, pp. 227–229.

Primary Examiner—Irene Marx
Attorney, Agent, or Firm—Oblon, Spivak, McClelland, Maier, & Neustadt

[57] ABSTRACT

The invention relates to a method of producing cyclosporin A and/or C which is characterized by culturing a cyclosporin A and/or C-producing strain of microorganism belonging to the genus Nectria (e.g. Nectria sp. F-4908) and recovering cyclosporin A and/or C from the resulting cultured broth.

2 Claims, 4 Drawing Sheets

PRODUCTION OF CYCLOSPORIN A AND/OR C WITH A STRAIN OF NECTRIA

DESCRIPTION

1. Technical Field

This invention relates to a method of producing cyclosporin A and/or C each having immunosuppressant, antiinflammatory and other activities. The invention finds application in the manufacture of drugs, among other things.

2. Background Art

The structures of cyclosporin A and C are disclosed in Helvetica Chimica Acta 59, 1075–1092 (1976), ditto 60, 1247–1255 (1977) and ditto 70., 13–36 (1987) and the technology for producing cyclosporin compounds, inclusive of cyclosporin A and C, are described in JP Kokai S-50-89598, JP Kokai S-52-59180, JP Kokai S-55-55150 and JP Kokai S-57-63093.

DISCLOSURE OF INVENTION

The inventors of this invention explored for a new technology for producing cyclosporin compounds and discovered that a new strain of microorganism of the genus Nectria(Fr.)Fr., which differentiates itself from any of the organisms employed in the above-mentioned prior art technology, is able to produce cyclosporin A and/or C. This invention is, therefore, directed to a method which comprises culturing a cyclosporin A and/or C-producing strain of microorganism of the genus Nectria and recovering cyclosporin A and/or C from the resulting cultured broth.

Among the cyclosporin A and/or C-producing strains belonging to the genus Nectria which can be employed in this invention, the strain (designated F-4908) which the inventors of this invention isolated from a soil sample collected in NaZe-shi, Amami Oh-shima, Kagoshima-ken, Japan has the following mycological characteristics.

Cultural characteristics on various media

Table 1 shows cultural characteristics of F-4908 on potato glucose agar, malt extract agar and corn meal agar after 2 weeks incubation at 25° C. The color descriptions used in this specification are based on the Color Standard issued by Japan Color Research Institute.

TABLE 1

| Cultural characteristics of F-4908 on various media | | | |
|---|---|---|---|
| | Potato glucose agar | Malt extract agar | Corn meal agar |
| Colony morphology | irregular | irregular to circular | Circular |
| Colony diameter | 1.5 cm | 1.5–2.0 cm | 2.5–3.0 cm |
| Colony surface | Wrinkled and raised, felt-like and covered with short flocci. | Wrinkled in center, plane, felt-like and covered with short flocci. | Plane and thin, aerial mycelium not rising. |
| Surface color | Light olive - olive or grayish olive. Orange-colored exudations produced at center. | Pale olive - light olive. | White. Yellow in center only. |
| Reverse color | Dark yellowish brown–dark brown. A brown soluble pigment diffusing into medium. | Yellowish brown. A yellow soluble pigment diffusing into medium. | White. Yellow in center only. |

TABLE 1-continued

| Cultural characteristics of F-4908 on various media | | | |
|---|---|---|---|
| | Potato glucose agar | Malt extract agar | Corn meal agar |
| Other characteristics | No spore formation in teleomorphic and anamorphic states. | No spore formation in teleomorphic and anamorphic states. | Conidia are formed on 2-week incubation at 25° C.. Perithecia are formed on 4-week or longer incubation at 25° C.. |

Physiological characteristics

The growth temperature range of F-4908 is 4–35° C. and the optimum temperature range for growth is 18–28° C. The growth pH range of the strain is pH 3–10 and the optimum pH range is pH 6–7.

The teleomorph(ascomata) of F-4908 is observed on corn meal agar at 25° C. after not less than 4 weeks, with the production of brown ascospores in the perithecia. The hyphal conidiomata is observed on various culture media. The conidiogenesis is enteroblastic (phialidic).

When the stain is inoculated on a plant leaf whose surface has been sterilized, the perithecia are superficial and globose, subglobose or ampule-shaped, with one papillate ostiole. There is no lateral hair, the color ranges from light brown to orange, and the diameter is 150–250 μm. The peridia are composed of 3 to 4 layers of thin-walled cells. The papillae are 70 to 80 μm in diameter and 50–60 μm high, and there are many periphyses inside the ostiole. The asci are unitunicate, cylindrical to clayate, eight-spored in a single row, 60–85 μm in length and 7.5–11 μm in width. Its apical structures develop poorly and they are not amyloid. The ascospores are tan to brown tuberculate to spinulose, two-celled each having one vacuole, 11–12 μm in length, 6–7 μm in width, ellipsoidal to broadly ellipsoidal, rounded at the ends and constricted at septa. The conidiophores are hyaline, smooth, septate, mononematous or forming loose coremia, 50–100 μm in length and 3–4.5 μm in width, with its opical cell forming phialides. The phialides are hyaline, smooth, cylindrical or filiform, with clearly terminal collarette, 30–45 μm long, 2–3.5 μm wide, and 1–2 μm thick at the tip. The conidia are one-celled, hyaline, smooth, and subprolate to prolate, and vary widely in length, i.e. 5–24μm, and in width, i.e. 2.5–4μm, and are non-catenate but form a small mass at the apex of the phialidelides.

The vegetative hyphae are septate, hyaline, smooth and branched. The hyphal cells are cylindrical with a width of 2–4.5 μm. The chlamydospores are absent.

Thus, F-4908 is considered to belong the ascomycete genus Nectria and its anamorph can be assigned to Acremonium Link or Acrocylindrium Bonorden. F-4908 is characterized in that the perithecia occur singly with no formation and produce tubeculate ascocarps and that the perithecium is thin. According to the Nectria taxonomic criteria described in Mycological Papers 73, 1–115 (1959), Mycologia 65, 401–420 (1973) and New Zealand Journal of Botany 14, 231–260 (1976), F-4908 relatively ressembles to Nectria peziza(Tode ex Fr.) Fr. or Nectria dentifera Samuels. However, Nectria peziza is distinct from F-4908 not only in the surface ornamentation that its ascospores are striate but also in the size of perithecium and the size, shape and pigmentation of ascospores. *Nectria dentifera* is further different from the strain of F-4908 in the surface ornamentation, size, shape and pigmentation of the ascospore, size of the ascus and shape of the perithecium. Therefore, it is considered that among the known microorganisms of the genus Nectria whose teleomorphs can be relegated to Acremonium or Acrocylindrium, there is no organism corresponding to F-4908.

Based on the above findings, F-4908 was considered to be a new strain belonging to genus Nectria and named Nectria sp. F-4908.

Nectria sp. F-4908 has been deposited with Fermentation Research Institute, Agency of Industrial Science and Technology, the Ministry of International Trade and Industry (1-3 Higashi 1-chome, Tsukuba-shi, Ibaraki-ken, Japan) under the accession number of FERM BP-3235 on 22th, Jan, Heisei 3 nen (1991).

The cyclosporin A and/or C producing activity of the cyclosporin A and/or C-producing strain of microorganism for use in this invention can be enhanced by subjecting the strain to a well-known mutagenic treatment such as irradiation with X-rays, ultraviolet light, etc., treatment with a chemical mutagen such as nitrogen mustard, azaserine, nitrous acid, 2-aminopurine, N-methyl-N'-nitro-N-nitrosoguanidine (NTG), etc., phage contacting, transformation, transduction, conjugation and so on.

Production of cyclosporin A and/or C by cultivation of a cyclosporin A and/or C-producing strain belonging to the genus Nectria can be carried out as a rule by the well-known method for culture of microorganisms in general, although submerged culture using a liquid medium is advantageous. The culture medium may be any medium that contains those sources of nutrients which the cyclosporin A and/or C-producing strain of the genus Nectria may utilize. Thus, a synthetic, semi-synthetic or natural medium can be utilized. As regards the components of the medium, carbon sources such as glucose, sucrose, maltose, glycerin, starch, soluble starch, etc. and nitrogen sources such as meat extract, casein hydrolysate, peptone, gluten meal, corn meal, cottonseed flour, soybean flour, corn steep liquor, peanut powder, wheat germ, dried yeast, yeast extract, urea, ammonium phosphate, etc. can be employed. In addition to these nutrients, inorganic salts such as disodium hydrogen phosphate, potassium dihydrogen phosphate, magnesium chloride, magnesium sulfate, calcium carbonate, sodium iodide, cobalt chloride 6 $H_2O$, etc. can be added as necessary.

If copious foaming occurs during culture, a defoaming agent such as vegetable oil, e.g. soybean oil, linseed oil, etc., higher alcohol, e.g. octadecanol, tetradecanol, heptanol, etc., or a silicone compound can be added as needed.

The preferred incubation temperature is about 25–30° C., and in many cases satisfactory results are obtained when seed culture is used depending on the required volume of culture. The incubation time is preferably about 50 to 300 hours but can be increased as the culture medium becomes thickened.

The cultural conditions can be optimized according to the characteristics of the producing strain used.

The cyclosporin A and/or C produced by culture is generally accumulated intracellularly or extracellularly, vizo in the liquid phase of the cultured broth. Generally speaking, the cultured broth is first separated into the cellular fraction and the liquid fraction (filtrate or supernatant) by filtration or centrifugation and, then, the object substance is isolated and purified by the well-known procedures for the production of antibiotics in general.

By way of illustration, the object substance cyclosporin A and/or C can be separated and purified by a method which comprises dissolving the cells in a solvent, extracting the object substance with a solvent, pooling the extract with the filtrate, subjecting the pooled fluid to an appropriate combination or repetition of purification procedures such as pH adjustment, treatment with an anion exchange resin, a cation exchange resin and/or a nonionic adsorbent resin, adsorption treatment with an adsorbent such as activated carbon, silicic acid, silica gel, alumina, cellulose, etc., crystallization and recrystallization.

The following example is further descriptive of this invention.

Three Erlenmeyer flasks of 500 ml capacity are respectively filled with 160 ml of a seed medium (pH 6.0) containing 2% of soluble starch, 1% of corn starch, 1% of glucose, 1% of cottonseed flour, 0.5% of yeast extract, 0.5% of peptone, 0.5% of corn steep liquor and 0.2% of calcium carbonate and, then, sterilized. Each flask is then inoculated with Nectria sp. F-4908 (FERM-BP 3235) and incubated at 25° C. for 96 hours to provide a seed culture.

Separately, a jar fermenter of 30 l capacity is filled with 20 l of a production medium (pH 6.5) containing 6% of soluble starch, 3% of corn steep liquor, 1% of peanut powder, 1% of yeast extract, 0.1% of Adekanol and 0.2% of calcium carbonate and, then, sterilized. The above seed culture is added to the sterilized medium and incubated at 25° C. for 168 hours (aeration 20 l/min , internal pressure 10 kg/$cm^2$, agitation 350 rpm). Upon completion of culture, Radiolite (trademark, Showa Kagaku Kogyo Co., Ltd.) (500 g) is added and the broth is filtered using a filter press to provide 13 l of a filtrate and a cellular cake.

To the cellular cake is added 7 l of acetone and the mixture is allowed to stand at room temperature for 2 hours, at the end of which time it is filtered to provide an acetone extract of cells. This acetone extract is combined with the filtrate previously obtained and the mixture is adsorbed on Diaion HP-20 (trademark, Mitsubishi Kasei Corporation) (2 l). The Diaion HP-20 is washed with water (4 l) and 50% acetone-water (4 l) in that order and elution is then carried out with acetone in 2 l fractions. Fraction 4 is concentrated under reduced pressure to remove the acetone. The residue is extracted with ethyl acetate (20 ml) twice and the extract is concentrated under reduced pressure to provide a brown oil. This oil is subjected to silica gel chromatography and serial elution is carried out with n-hexane (100 ml), n-hexane-ethyl acetate (1:1 v/v, 160 ml), n-hexane-ethyl acetate (1:2 v/v, 200 ml), ethyl acetate (300 ml) and acetone (100 ml), the eluate being collected in 20 ml fractions.

Fractions 24 to 27 are pooled and concentrated under reduced pressure to provide cyclosporin A (196 mg).

Then, fractions 37 to 40 are pooled and concentrated under reduced pressure. The residue (55 mg) is dissolved in 85% methanol-water and purified using an NS Gel (Nippon Fine Chemical Co., Ltd. ) column (30 ml) to provide cyclosporin C (34 mg). The $H^1$ nuclear magnetic resonance spectrum and infrared absorption spectrum of the cyclosporin A obtained above are shown in FIGS. 1 and 3, respectively. The measured physicochemical constants of this substance were in good agreement with those of cyclosporin A as given in Helvetica Chimica Acta 59, 1075–1092 (1976) and ditto 70, 13–36 (1987). The $^1$H nuclear magnetic resonance spectrum and infrared absorption spectrum of the cyclosporin C are shown in FIGS. 2 and 4, respectively. The physicochemical data on this substance were in good agreement with those mentioned for cyclosporin C in Helvetica Chimica Acta 60, 1247–1255 (1977) and ditto 70, 13–36 (1987).

BRIEF DESCRIPTION OF DRAWINGS

FIG. 1 shows the $^1$H nuclear magnetic resonance spectrum of cyclosporin A, FIG. 2 shows the $^1$H nuclear magnetic resonance spectrum of cyclosporin C, FIG. 3 shows the infrared absorption spectrum of cyclosporin A and FIG. 4 shows the infrared absorption spectrum of cyclosporin C.

Figure 1:
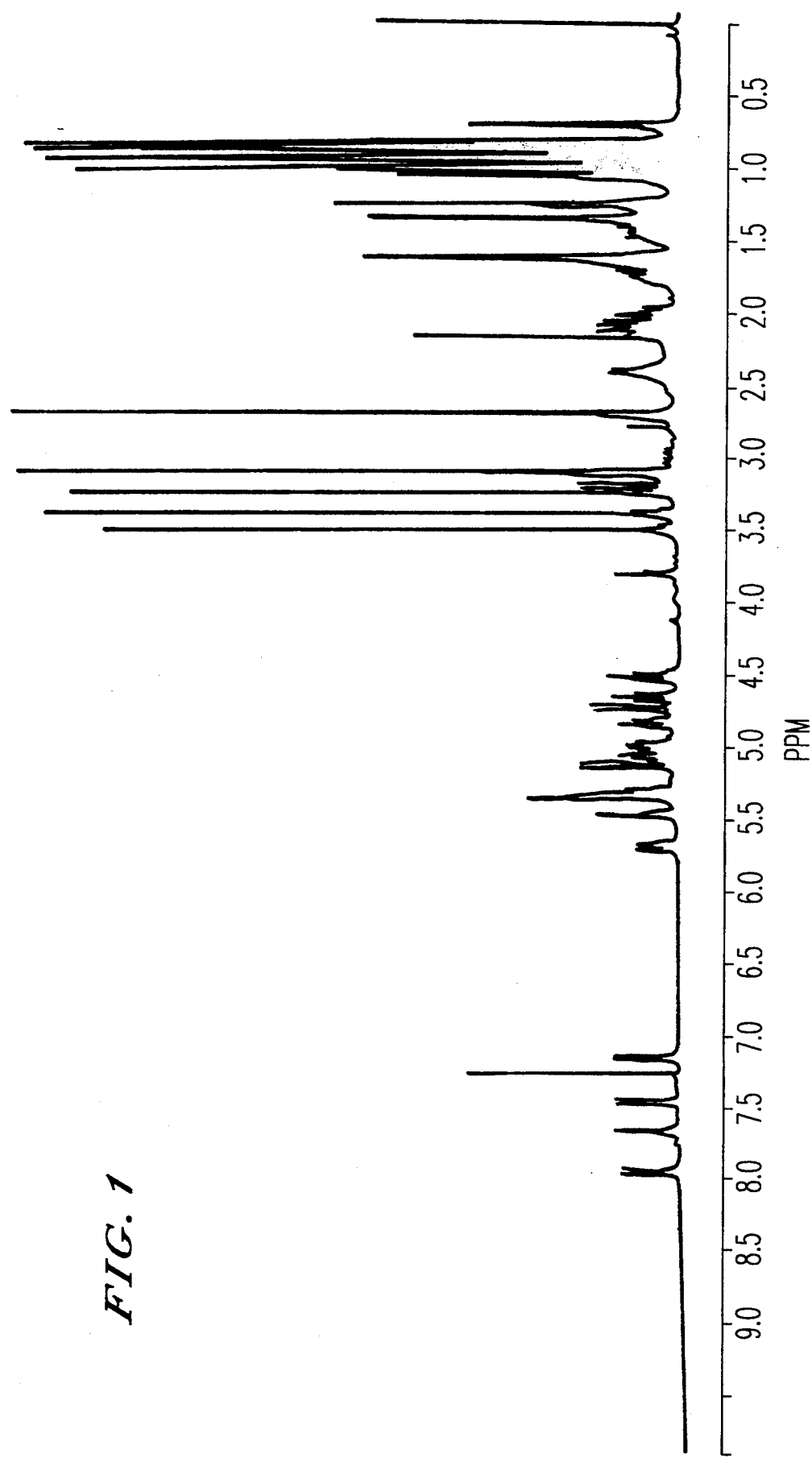
FIGS. 1 to 4 show the $^1$H nuclear magnetic resonance spectra and infrared absorption spectra of cyclosporin A and C as provided by this invention.
Figure 2:
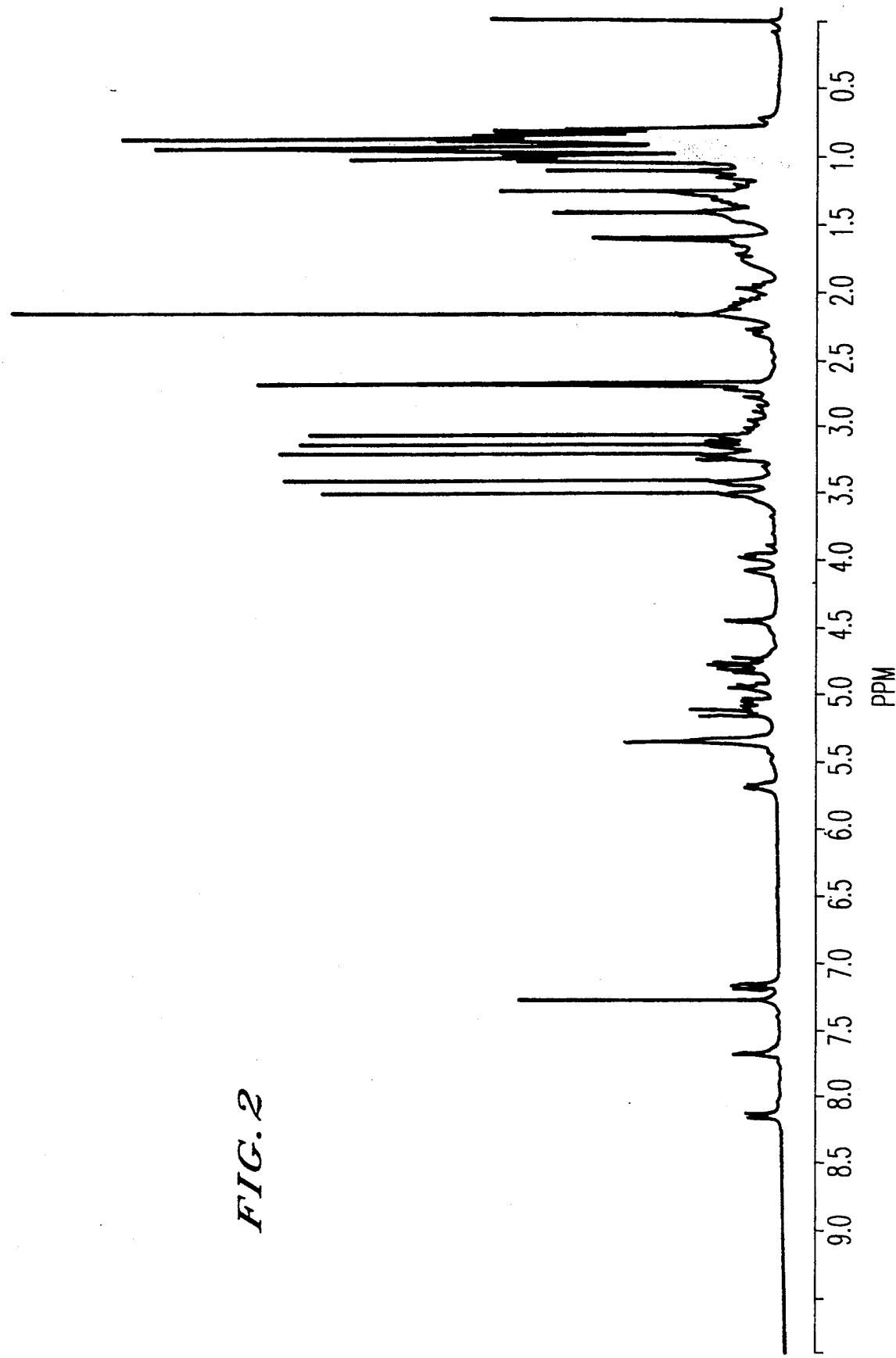
Figure 3:
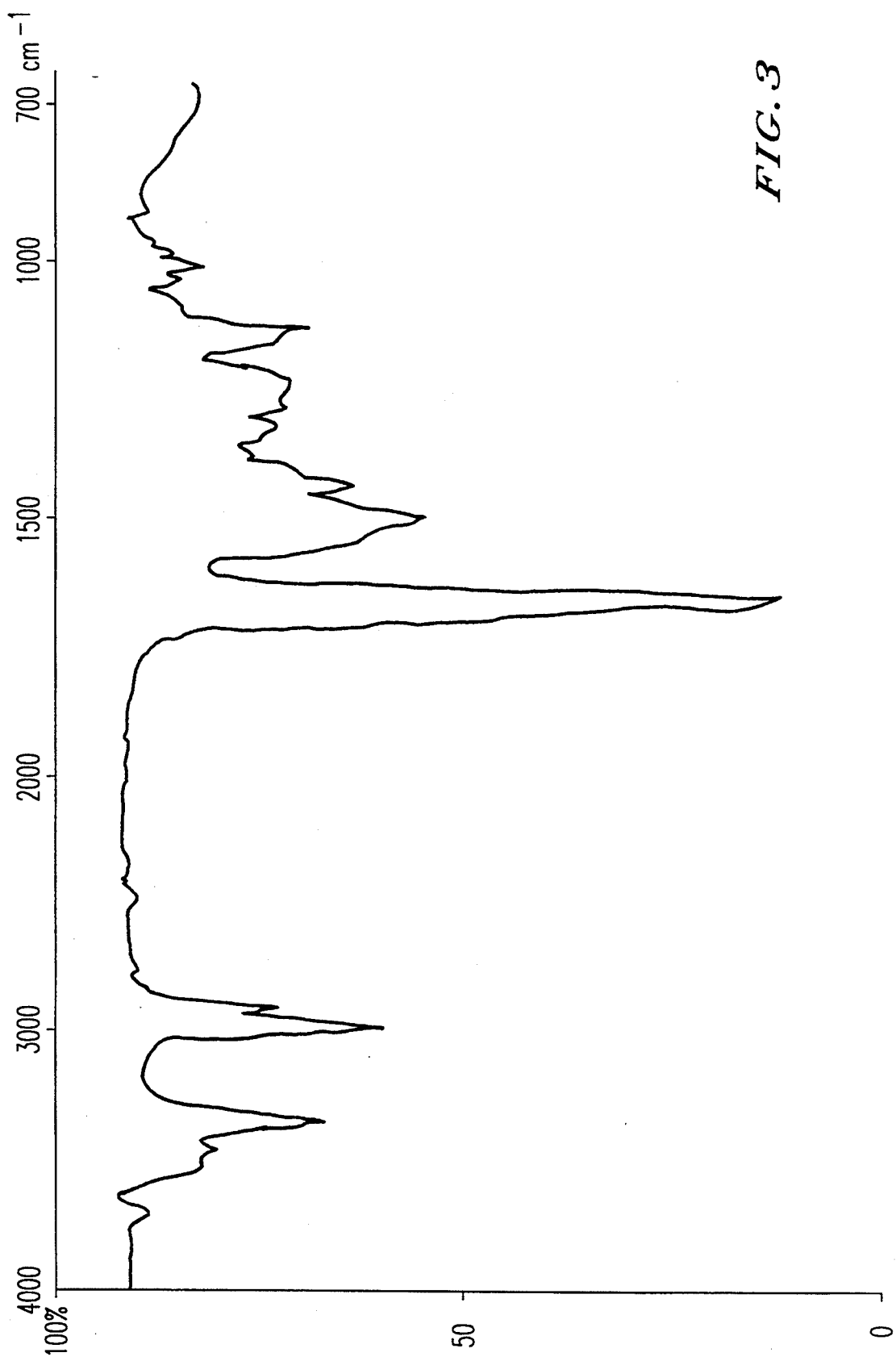
Figure 4:
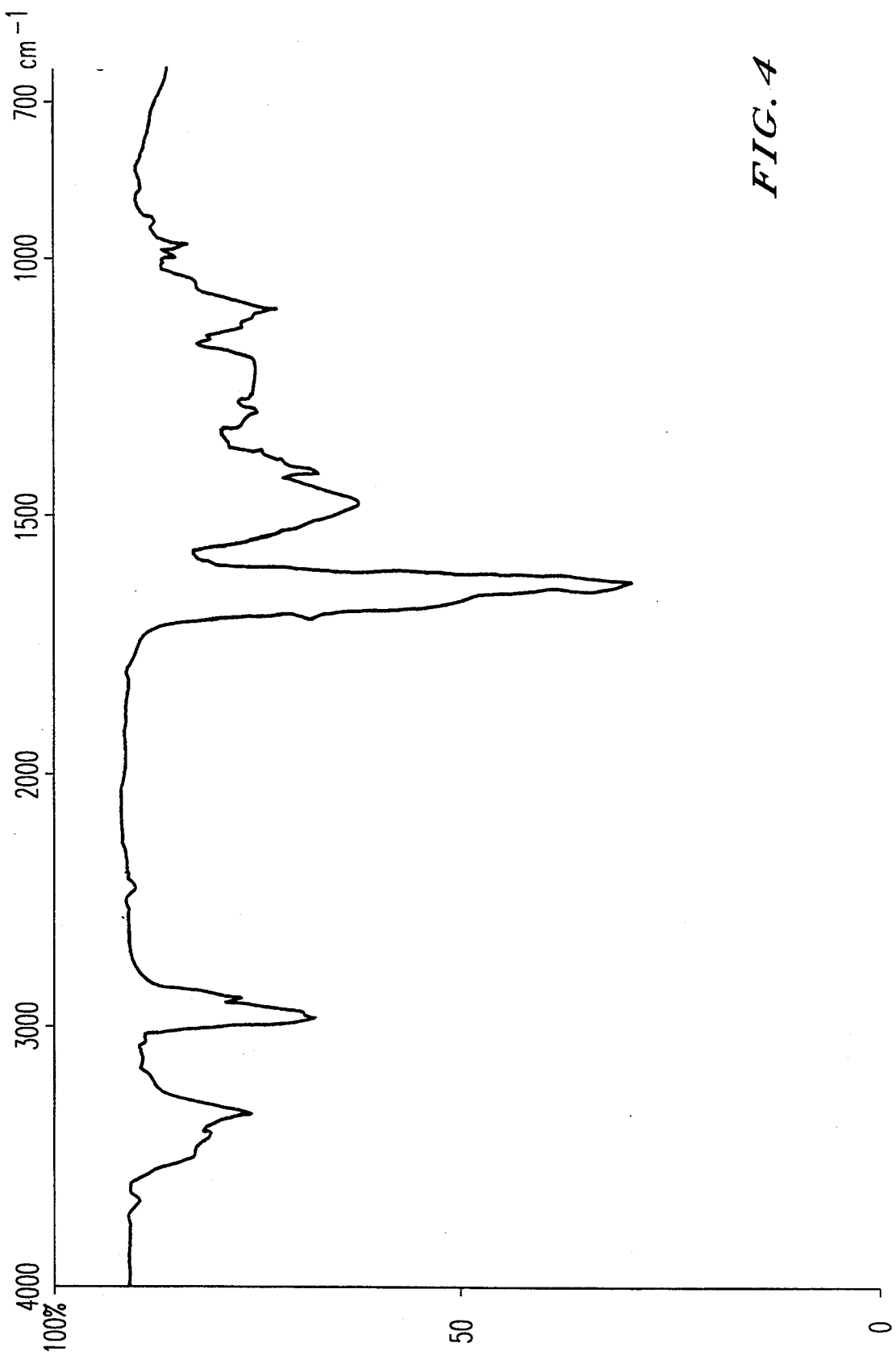

We claim:

1. A biologically pure culture of Nectria sp. F-4908.
2. A method of producing cyclosporin A and/or C which comprises culturing Nectria sp. F-4908 in a medium capable of supporting this strain and recovering cyclosporin A and/or C from the resulting cultured broth.

* * * * *